(12) United States Patent
Kurosawa

(10) Patent No.: US 6,929,605 B2
(45) Date of Patent: Aug. 16, 2005

(54) LIGHT SOURCE DEVICE WITH DUAL ALTERNATELY-DIRECTED LAMPS THAT FACILITATE LAMP REPLACEMENT

(75) Inventor: Hidehito Kurosawa, Tokyo (JP)

(73) Assignee: PENTAX Corporation, Tokyo (JP)

( * ) Notice: Subject to any disclaimer, the term of this patent is extended or adjusted under 35 U.S.C. 154(b) by 197 days.

(21) Appl. No.: 10/401,609

(22) Filed: Mar. 31, 2003

(65) Prior Publication Data

US 2003/0187329 A1 Oct. 2, 2003

(30) Foreign Application Priority Data

Apr. 1, 2002 (JP) ..................................... P2002-098717

(51) Int. Cl.⁷ ................................................ A61B 1/06
(52) U.S. Cl. ..................................... 600/178; 362/574
(58) Field of Search ............................... 362/233, 250, 362/285, 287, 289, 368, 371, 572, 574; 600/160, 178, 249

(56) References Cited

U.S. PATENT DOCUMENTS

| | | | | |
|---|---|---|---|---|
| 1,844,651 A | * | 2/1932 | Halvorson | 362/427 |
| 2,097,250 A | * | 10/1937 | Keith | 340/331 |
| 3,692,993 A | * | 9/1972 | Robinson | 362/250 |
| 3,831,017 A | * | 8/1974 | Auer | 362/572 |
| 3,878,389 A | * | 4/1975 | Puyplat | 362/233 |
| 4,110,820 A | * | 8/1978 | Konoshima | 362/207 |
| 4,135,231 A | * | 1/1979 | Fisher | 362/269 |
| 4,225,906 A | * | 9/1980 | Gulliksen et al. | 362/254 |
| 4,386,391 A | * | 5/1983 | Gulliksen et al. | 362/232 |
| 4,402,038 A | * | 8/1983 | Hartung et al. | 362/20 |
| 4,415,951 A | * | 11/1983 | Recane et al. | 362/20 |
| RE31,987 E | * | 9/1985 | Hartung et al. | 362/20 |
| 4,757,426 A | * | 7/1988 | Scheller et al. | 362/20 |
| 4,764,854 A | * | 8/1988 | Matsune et al. | 362/226 |
| 4,795,388 A | * | 1/1989 | Coliandris et al. | 445/22 |
| 4,855,875 A | * | 8/1989 | Onose et al. | 362/572 |
| 4,899,264 A | * | 2/1990 | Ries et al. | 362/92 |
| 4,943,895 A | * | 7/1990 | Brandenburg | 362/527 |
| 5,394,316 A | * | 2/1995 | Holbrook et al. | 362/294 |
| 5,893,632 A | * | 4/1999 | Kusagaya et al. | 362/226 |
| 6,132,069 A | * | 10/2000 | Sato et al. | 362/365 |

FOREIGN PATENT DOCUMENTS

| | | |
|---|---|---|
| JP | 7-27012 | 5/1995 |
| JP | 10-192238 | 7/1998 |
| JP | 2883083 | 2/1999 |
| JP | 2000-139836 | 5/2000 |

* cited by examiner

Primary Examiner—John Leubecker
Assistant Examiner—Philip R Smith
(74) Attorney, Agent, or Firm—Greenblum & Bernstein, P.L.C.

(57) ABSTRACT

A light-source device for an endoscope includes a housing, first and second lamps, and first and second movable lamp mounting sections. The first movable lamp-mounting section is transferable with respect to the housing between first and second lamp positions. The second movable lamp-mounting section is attached to the first movable lamp-mounting section and is transferable between a lighting position and a lamp replacing position. The first lamp is optically connected to a light guide cable when the second movable lamp-mounting section is positioned at the lighting position and when the first movable lamp-mounting section is positioned at the first lamp position. The second lamp is optically connected to the light guide cable when the second movable lamp-mounting section is positioned at the lighting position and when the first movable lamp-mounting section is positioned at the second lamp position.

6 Claims, 17 Drawing Sheets

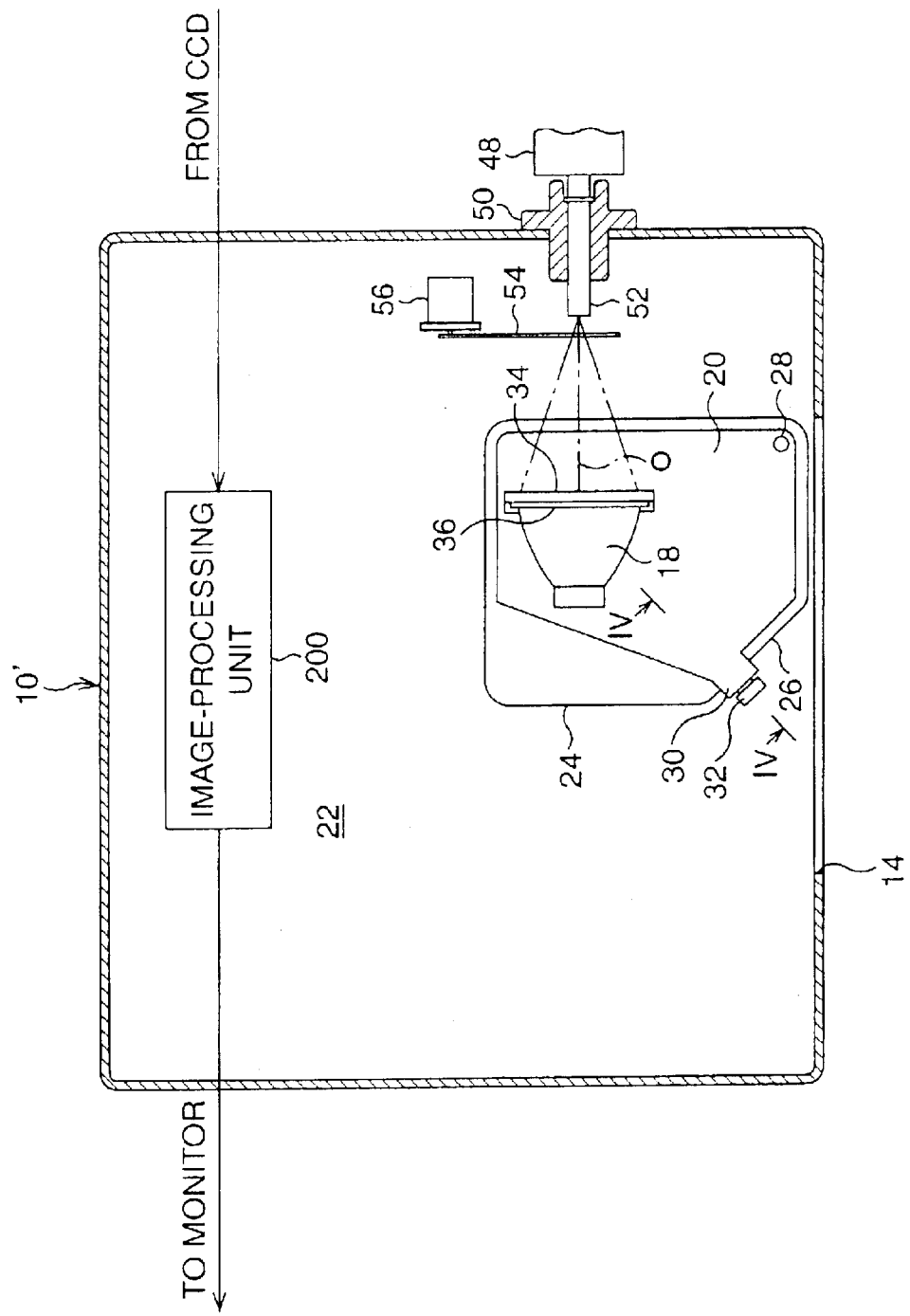

LIGHT SOURCE DEVICE WITH DUAL ALTERNATELY-DIRECTED LAMPS THAT FACILITATE LAMP REPLACEMENT

BACKGROUND OF THE INVENTION

1. Field of the Invention

The present invention relates to a light-source device for an endoscope. More particularly, the present invention relates to a light-source for an endoscope, that comprises at least two lamps, and which is structured so that a burn out lamp can be exchanged with a new lamp.

2. Description of the Related Art

As is well known, an endoscope, in which an internal image is observed through an optical fiber scope, and an electronic endoscope, in which an internal image is reproduced on a TV monitor, both require a light-source device or an image-signal processing apparatus that is provided with a light-source device into which an image-signal processing unit is integrated. This is because endoscopy carried out by inserting an optical fiber scope or an electronic endoscope into a human body requires light to illuminate the internal organs.

Therefore, inside the optical fiber scope and the electronic endoscope, a light guide cable for transmitting illumination light is provided. The incident end of the light guide cable is optically connected to the light-source device, and the emitting end of the light guide cable is connected to an illumination optical system disposed at the distal end of the optical fiber scope and the electronic endoscope. Accordingly, the illumination light transmitted from the light-source device through the light guide cable is emitted from the distal end of the optical fiber scope or the electronic endoscope.

As a lamp of the light-source device of the endoscope, a white-light lamp, such as a halogen lamp, a xenon lamp, and the like, is used. When the lamp is burnt out during the endoscope observation, of course the observation is disabled, so that diagnosis using the endoscope or the electronic endoscope is interrupted. This interruption of the diagnosis imposes a burden on a patient and also makes the diagnosis inefficient, so that it should be avoided as far as possible. Particularly, although the price of a halogen lamp is cheaper than that of a xenon lamp, the life of a halogen lamp is considerably shorter, therefore when a halogen lamp is used, the above problem is matter of grave concern.

Accordingly, as disclosed in KOKAI No. 7-27012, a light-source device for an endoscope that is provided with two lamps, which can be switched from the first lamp to the second lamp immediately when the first lamp is burnt out, is already proposed. In this type of light-source device, the two lamps are provided on a turntable that is rotatably switched between the first position and the second position. When the position of the turntable is rotated and switched from the first position to the second position, the second lamp is optically connected to the light-source device and turned on. According to the above light-source device, the diagnosis can be substantially continued without interruption even when the first lamp is burnt out.

SUMMARY OF THE INVENTION

However, the conventional light-source device is structured with out regard to the lamp replacement operation. Therefore, an object of the present invention is to provide a light-source device for an endoscope that is structured so that the lamp can be replaced swiftly and efficiently.

Another aspect of the present invention is to provide a light-source device for an endoscope that is provided with at least two lamps, and that is structured so that either of the lamps can be replaced or changed with the other lamp swiftly and efficiently when one lamp is burnt out.

According to the present invention, a light-source device for an endoscope is provided that comprises a housing, a lamp, and a movable lamp-mounting section.

A lamp replacement opening is formed in the housing. The lamp is mounted inside the housing, and mounted on the movable lamp-mounting section. The movable lamp-mounting section is transferable with respect to said housing between a lighting position and a lamp replacing position. When the movable lamp-mounting section is positioned at the lighting position, the lamp can be optically connected to a light guide cable, which transmits illumination light to the endoscope. The lamp is positioned outside the housing when the movable lamp-mounting section is pulled out to the lamp replacing position through the lamp replacement opening.

Further, according to the present invention, a light-source device for an endoscope is provided that comprises a housing, first and second lamps, and first and second lamp-mounting sections.

A lamp replacement opening is formed in the housing. The first lamp and a second lamp are mounted inside the housing and mounted on the second movable lamp-mounting section. The first movable lamp-mounting section is transferable with respect to the housing between a first lamp position and a second lamp position. The second movable lamp-mounting section is attached to the first movable lamp-mounting section in such manner that the second movable lamp-mounting section is transferable with respect to the first movable lamp-mounting section between a lighting position and a lamp replacing position. The first lamp can be optically connected to a light guide cable, which transmits illumination light to the endoscope, when the second movable lamp-mounting section is positioned at the lighting position and when the first movable lamp-mounting section is positioned at the first lamp position. The second lamp can be optically connected to the light guide cable when the second movable lamp-mounting section is positioned at the lighting position and when the first movable lamp-mounting section is positioned at the second lamp position. Further, the first and second lamps are pulled out to the outside of the housing when the second movable lamp-mounting section is pulled out to the lamp replacing position through the lamp replacement opening.

Furthermore, according to the present invention, an image-signal processing apparatus for an electronic endoscope is provided that comprises an image-signal processing unit, a housing, a lamp, and a movable lamp-mounting section.

The image-signal processing unit processes image-signals from the electronic endoscope. A lamp replacement opening is formed in the housing. The lamp is mounted inside the housing, and mounted on the movable lamp-mounting section. The movable lamp-mounting section is transferable with respect to said housing between a lighting position and a lamp replacing position. When the movable lamp-mounting section is positioned at the lighting position, the lamp can be optically connected to a light guide cable, which transmits illumination light to the endoscope. The lamp is positioned outside the housing when the movable lamp-mounting section is pulled out to the lamp replacing position through the lamp replacement opening.

BRIEF DESCRIPTION OF THE DRAWINGS

The objects and advantages of the present invention will be better understood from the following description, with reference to the accompanying drawings in which:

FIG. 17 is a cross sectional view of an electronic endoscope image-signal processing apparatus which includes the light-source device and an image-processing unit.

DESCRIPTION OF THE PREFERRED EMBODIMENTS

Figure 1:
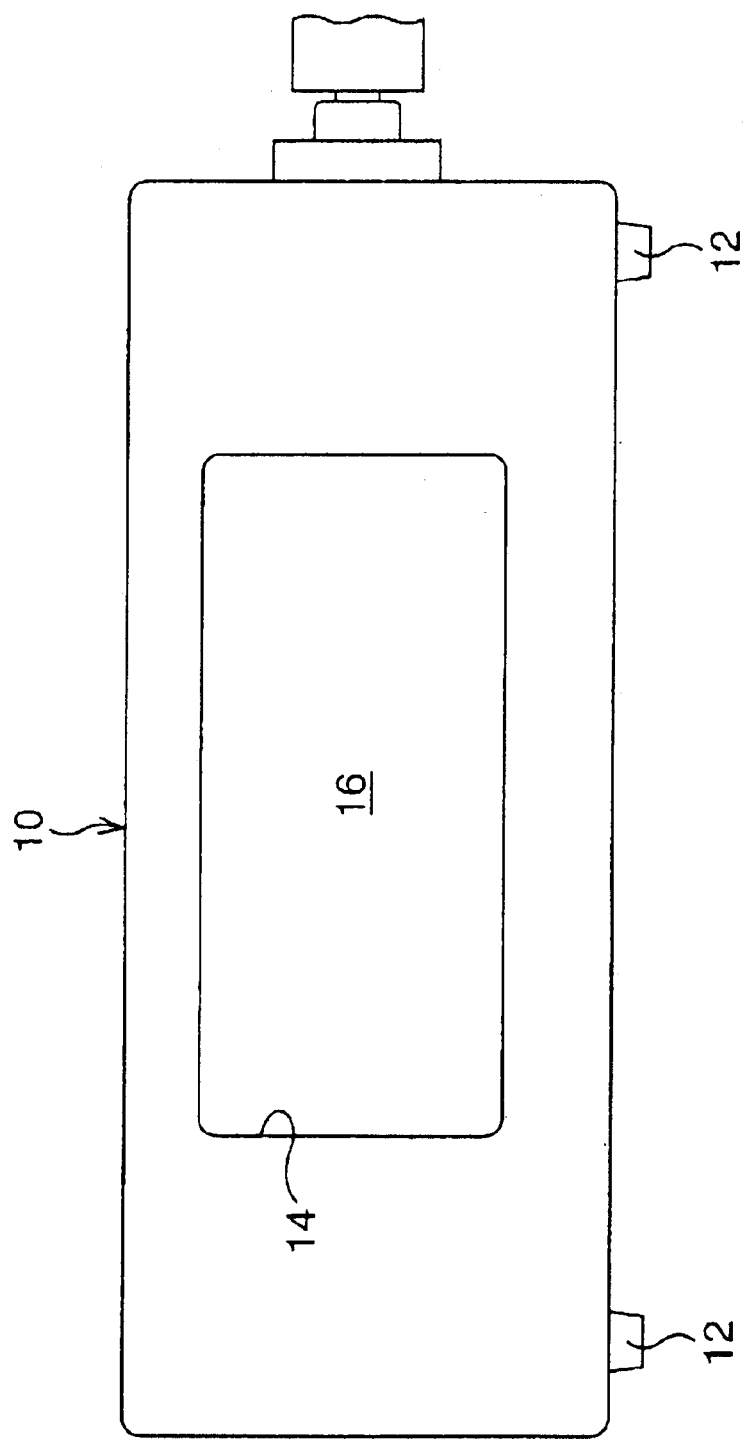
FIG. 1 is a side view of a light-source device of the first embodiment of the present invention.

The present invention is described below with reference to the embodiments shown in the drawings.

With reference to FIG. 1 to FIG. 7, a light-source device for an endoscope of the first embodiment of the present invention will be described.

Figure 2:
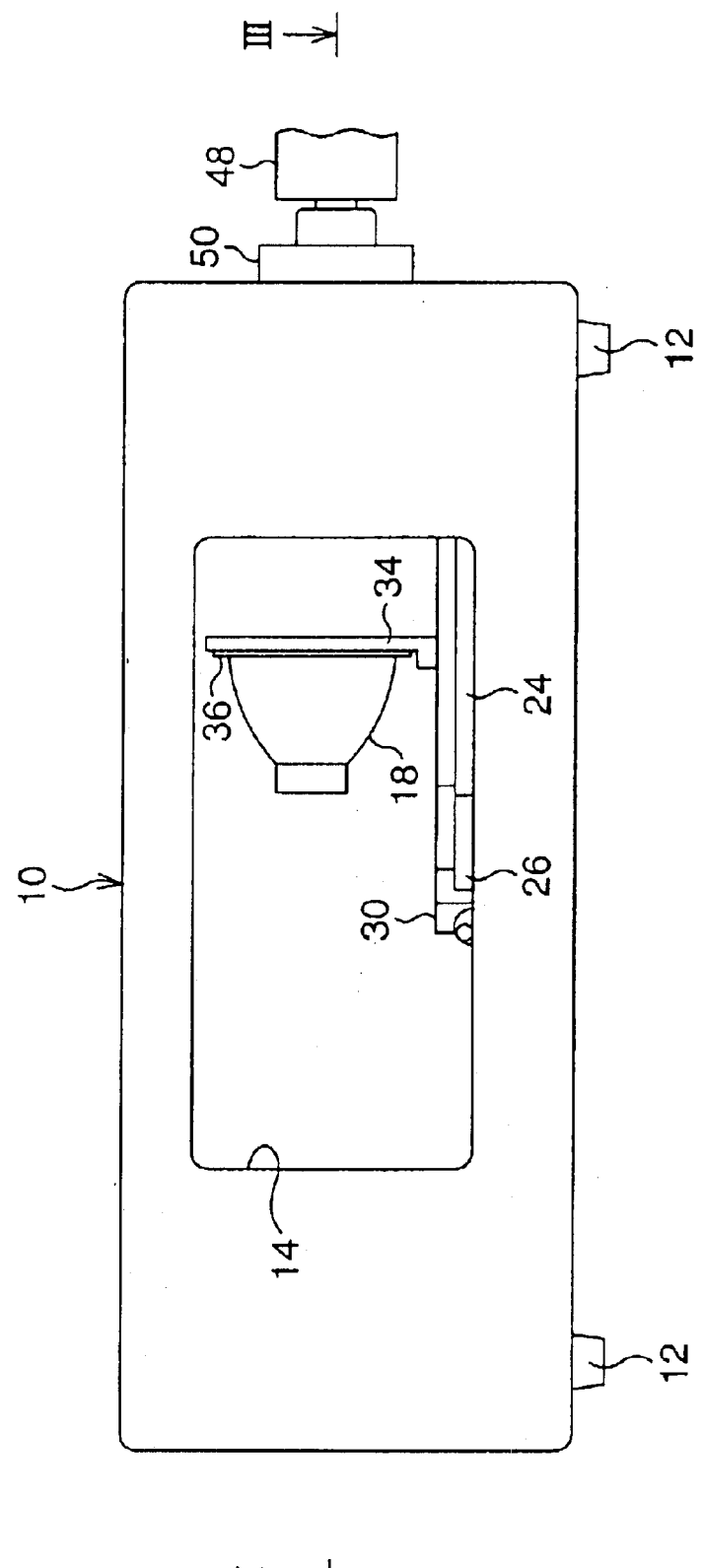
FIG. 2 is a side view of the light-source device in FIG. 1 with its window cover replaced and where the light-source unit inside the housing is visible.

The light-source device has a square-shape housing 10. As shown in FIG. 1 and FIG. 2, each of the four corners of the bottom surface of the housing 10 has hard rubber pads 12. On a sidewall of the housing 10, a lamp replacement window 14 is formed. Usually, the lamp replacement window 14 is covered with a window cover 16, as shown in FIG. 1, however, the window cover 16 is removed from the window 14 when it comes to replacing a lamp, when the endoscope is not being used, so that a user can access the inside of the housing 10 as shown in FIG. 2.

Figure 3:
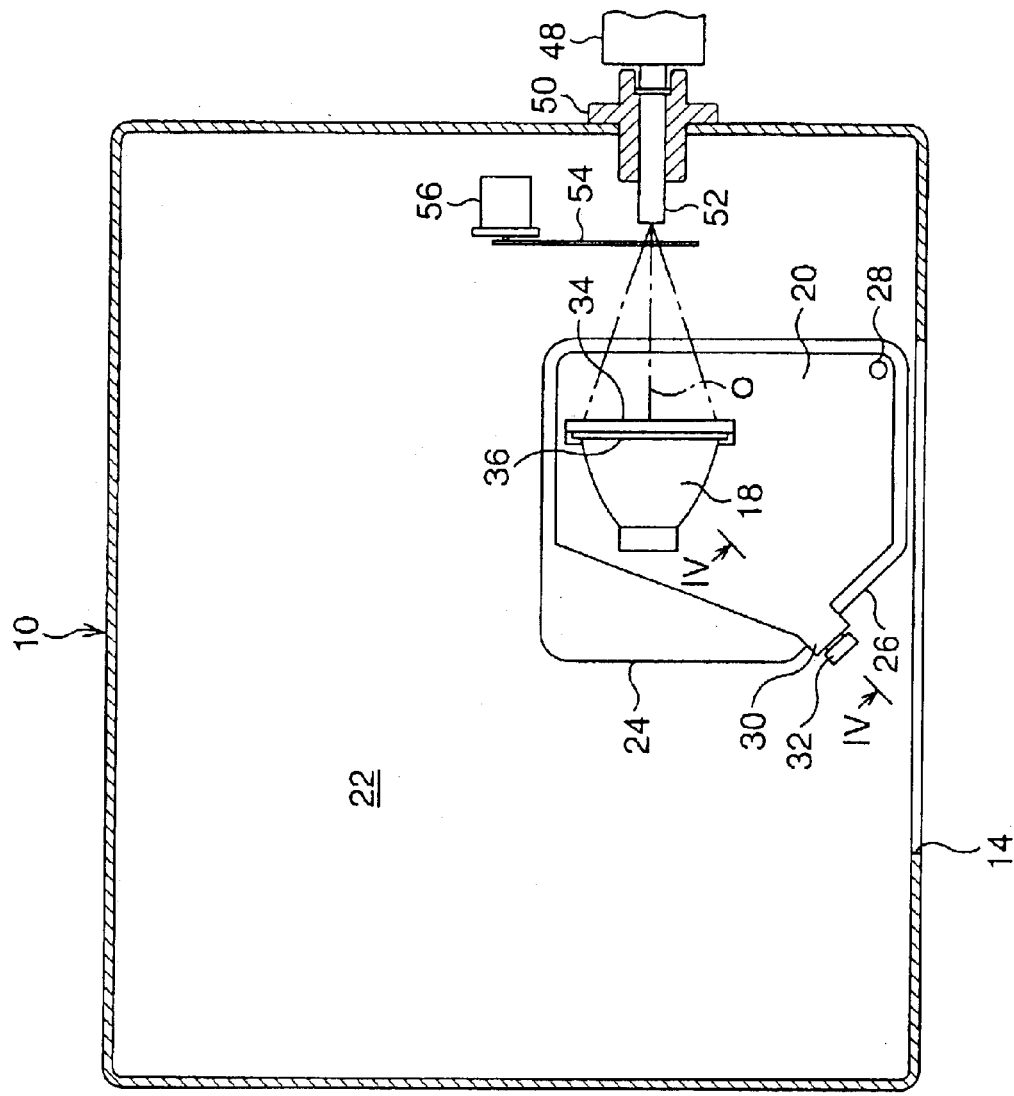
FIG. 3 is a cross sectional view of the light-source device along a line III—III of FIG. 2.

In FIG. 3, the light-source device is shown as a cross sectional view in which the housing 10 is sectioned along line III—III of FIG. 2. As is clear from FIG. 2 and FIG. 3, a white-light lamp 18, for example a halogen lamp, xenon lamp, or the like, is provided. The white-light lamp 18 is appropriately mounted on a movable lamp-mounting section 20. In the first embodiment, the movable lamp-mounting section 20 is arranged on a fixed stage 24 that is fixed on the bottom inner surface 22 of the housing 10.

Note that, although it is not described in FIG. 3, a power source unit that supplies electric power to the white-light lamp is provided inside the housing 10, and the power source obtains the power from a commercial power supply.

The fixed stage 24 is formed as a thick block member with a rectangular like shape. Namely, the outline of the fixed stage 24 of the thick block member is configured in the rectangular like shape from which one corner is removed. In FIG. 2 and FIG. 3, the removed side face, that is inclined with respect to the lamp replacement window 14, is indicated with the numeral 26. On the other hand, the movable lamp-mounting section 20 is formed as a thin board member having the outline shown in FIG. 3. The movable lamp-mounting section 20 is journalled to the fixed stage 24 with a pivot shaft 28 at a corner of the movable lamp-mounting section 20. Namely, the movable lamp-mounting section 20 is rotatable about the pivot shaft 28 on the fixed stage 24.

Figure 4:
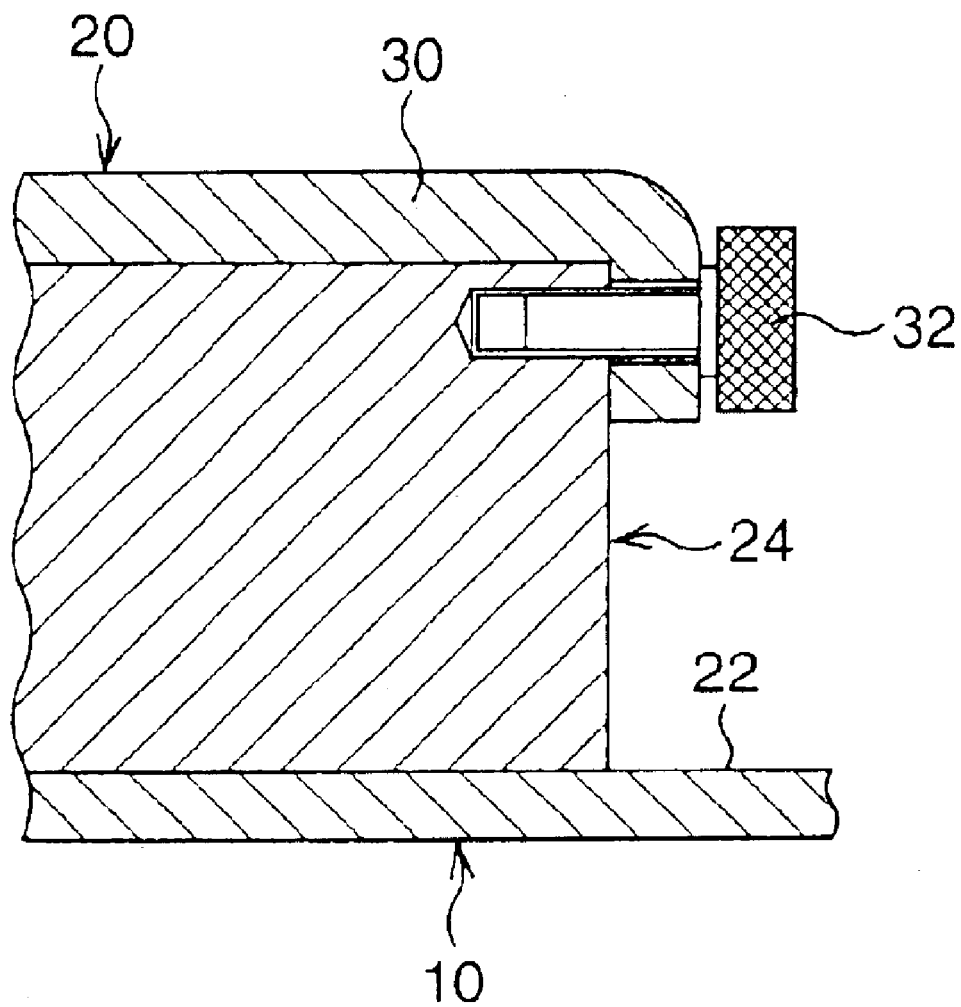
FIG. 4 is magnified sectional elevational view showing the mechanism for fastening the movable lamp-mounting section to the fixed stage along a line IV—IV of FIG. 3.

As is obvious form FIG. 3 and FIG. 4, a tongue piece member 30 extends out from the movable lamp-mounting section 20 and its end is bent downward. When the movable lamp-mounting section 20 is disposed at the lighting position (the position in which the white lamp 18 is turned on inside the housing 10), which is shown in FIG. 3, the end or the downwardly bent portion of the tongue piece 30 contacts with the removed side face 26 of the fixed stage 24. At the downwardly bent portion of the tongue piece 30, there is formed a through-hole through which a fastening screw 32 is inserted. The fastening screw 32 is screwed into a screw hole formed on the replaced side face 26 of the fixed stage 24 via the through-hole, and fastened. Thereby, the movable lamp-mounting section 20 is fixed at the lighting position with respect to the fixed stage 24, as shown in FIG. 3.

As it is suitably illustrated in FIG. 4, the fastening screw 32 has a head with a large diameter, so that the fastening screw 32 can be screwed by operator's fingers in the fastening or loosening operations. To make the operation definite and easy, a serration for preventing slipping may be arranged on the periphery of the head as shown in FIG. 4. Namely, the fastening screw 32 fulfills the fixing function whereby to fix the movable lamp-mounting section 20 releasably at the lighting position indicated in FIG. 3.

Figure 5:
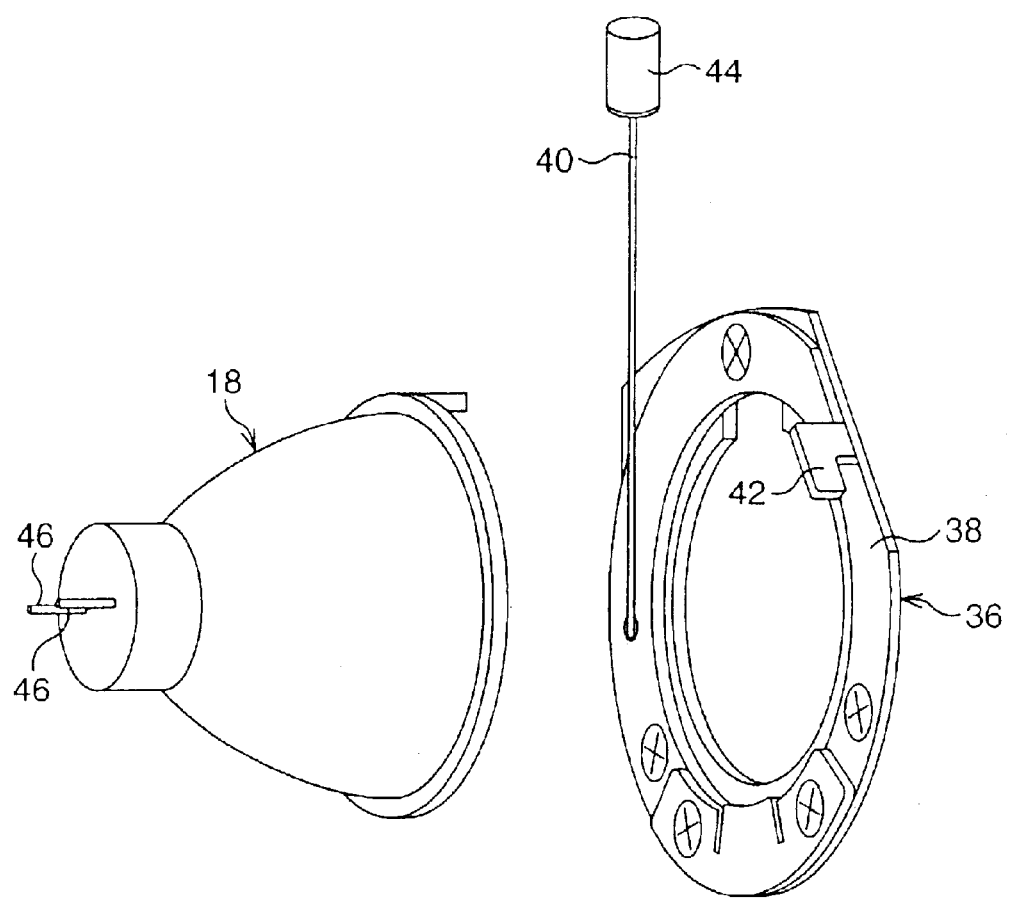
FIG. 5 is a perspective view of a white lamp and a fitting member before fitting the white lamp to the fitting member.
Figure 6:
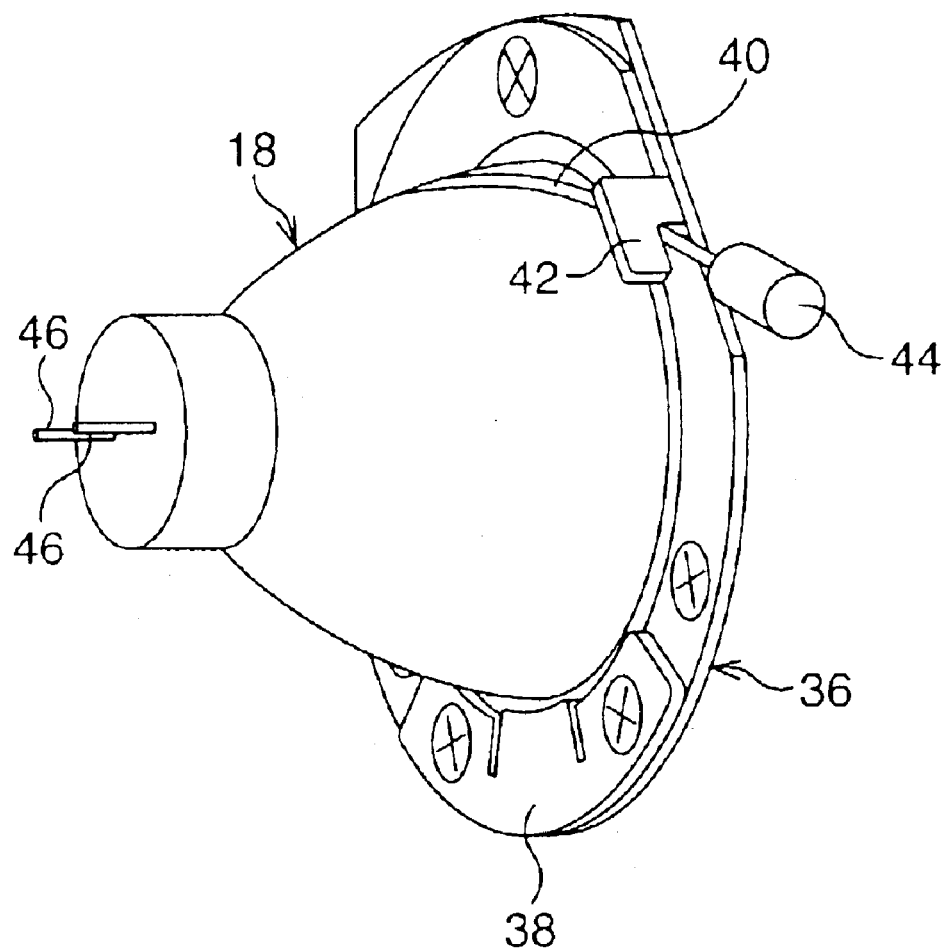
FIG. 6 is a perspective view of the white lamp and the fitting member after fitting the white lamp to the fitting member.

A lamp lamp-mounting frame 34 for mounting the white lamp 18 on the movable lamp-mounting section 20 is fixedly attached to the movable lamp-mounting section 20. The lamp-mounting frame 34 is integrated with a fitting member 36 as shown in FIG. 5 and FIG. 6. The fitting member 36 is comprised of a ring member 38, a piano wire 40, and a hook 42. The ring member 38 suitably engages with the front flange of the white lamp 18. The piano wire extends out from a certain appropriate position of the ring member 38. The hook 42 is formed at a certain appropriate position on the ring member 38. Note that, at the end of the piano wire 40, a pinch 44 is attached.

As is obvious from FIG. 5 and FIG. 6, for mounting the white lamp 18 on the fitting member 36, the front flange of the white lamp 18 is at first engaged with the ring member 38, and then the piano wire 40 is elastically deformed along the back side of the front flange and hooked on the hook 42. Thereby, the front flange is pressed against the ring member 38 by the piano wire 40 that engages with the back side of the front flange, and the mounting of the white lamp 18 on the fitting member 36 is complete. Of course the deformation of the piano wire 40 and the hooking of the piano wire 40 to the hook 42 is carried out by an operator by using the pinch 44.

As described in FIG. 5 and FIG. 6, a pair of electrode plugs 46 protrudes out from the back end of the white lamp 18, so that the pair of electrode plugs 46 is detachably plugged into an outlet socket (not shown). The outlet socket is connected to the above power source unit via an electric cord. Note that, a lamp power switch is provided on the outer surface of the housing 10 at a certain appropriate position. Namely, the ON/OFF states of the power supply from the power source unit via the outlet socket to the white lamp 18 is controlled by the power switch, so that the ON/OFF state of the white lamp 18 is controlled.

As described in FIG. 3, a connector 50 for connecting the light guide cable 48 of an endoscope is attached to the sidewall of the housing 10. In detail, the light guide cable 48 is comprised of an optical fiber bundle and a cable coverture covers the optical fiber bundle. At the incident end of the light guide cable 48, an optical guide rod 52 is optically connected, so that the light guide cable 48 is optically connected to the light-source device when the optical guide rod 52 is plugged into the center of the connector 50.

Inside the white lamp 18, a concaved reflecting mirror is installed. In FIG. 3, the optical axis of the concaved reflecting mirror is indicated by a reference symbol O. When the movable lamp-mounting section 20 is placed at the lighting position, as shown in FIG. 3, the optical axis O of the concaved reflecting mirror of the white lamp 18 coincides with the central axis of the connector 50. Therefore, when the optical guide rod 52 is plugged into the connector 50 and being connected thereto, the optical axis of the optical guide rod 52 is made coaxial with the optical axis O of the concaved reflecting mirror of the white lamp 18. Further, the opening of the white lamp 18 is provided with a condensing lens. The optical axis of the condensing lens is made coaxial with the optical axis O of the concaved reflecting mirror. Thereby, when the optical guide rod 52 is connected to the connector 50, the distal end of the optical guide rod 52 is positioned at the focal point of the above condensing lens. Accordingly, the light emitted from the white lamp 18 is efficiently concentrated upon the end face of the optical guide rod 52 and made incident thereto.

As shown in FIG. 3, a stop blade 54 is disposed between the white lamp 18 and the end face of the optical guide rod 52. The stop blade 54 is operated by a certain appropriate actuator 56. Namely, the diameter of the aperture for the illumination light beam, which is controlled by the stop blade 54, is adjusted by the operation of the actuator 56. Thereby, the amount of the illumination light which is incident on the optical guide rod 52 from the white lamp 18 is adjusted. Note that, the operation of the actuator 56 is appropriately controlled by a control circuit board installed inside the housing 10.

In the following, how the white lamp 18 in the above light-source device is replaced will be explained.

Figure 7:
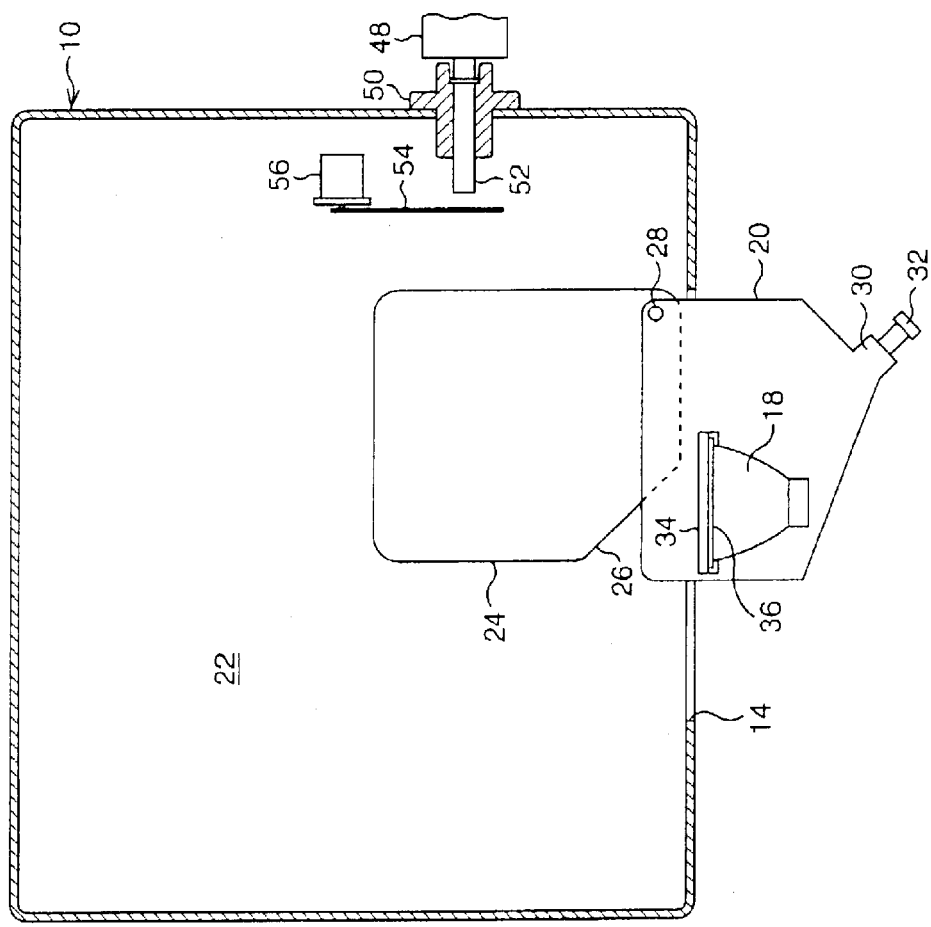
FIG. 7 is a cross sectional view of the light-source device along a line III—III of FIG. 2 with the movable lamp-mounting section at the lamp replacing position.

In the beginning, the lamp power switch is turned off so as to safely carry out the replacement. The window cover 16 is then removed from the housing 10, so that the movable lamp-mounting section 20 can be accessed through the lamp replacement window 14. The fastening screw 32 is then detached from the screw hole by a manual unfastening operation. When the movable lamp-mounting section 20 is rotated about the pivot shaft 28 by pulling the end portion of the tongue piece 30 outwardly, the movable lamp-mounting section 20 is moved to the lamp replacing position as shown in FIG. 7 from the lighting position in FIG. 3. As is obvious from FIG. 7, the white lamp 18 is pulled out to the outside of the housing 10 with the movable lamp-mounting section 20 through the lamp replacement window 14.

Thereby, the white lamp 18 can be replaced by a new one quite easily by pulling out the white lamp 18 to the outside of the housing 10. A new white lamp 18 is ready to use, when the movable lamp-mounting section 20 is returned to the lighting position by carrying out the above processes in reverse after the white lamp 18 has been replaced by the new one.

Next, with reference to FIG. 8 to FIG. 16, a light-source device of the second embodiment of the present invention is explained. Note that, in FIG. 8 to FIG. 16, components which are similar to those in the first embodiment are referred to using the same numerals as those in the first embodiment.

Figure 8:
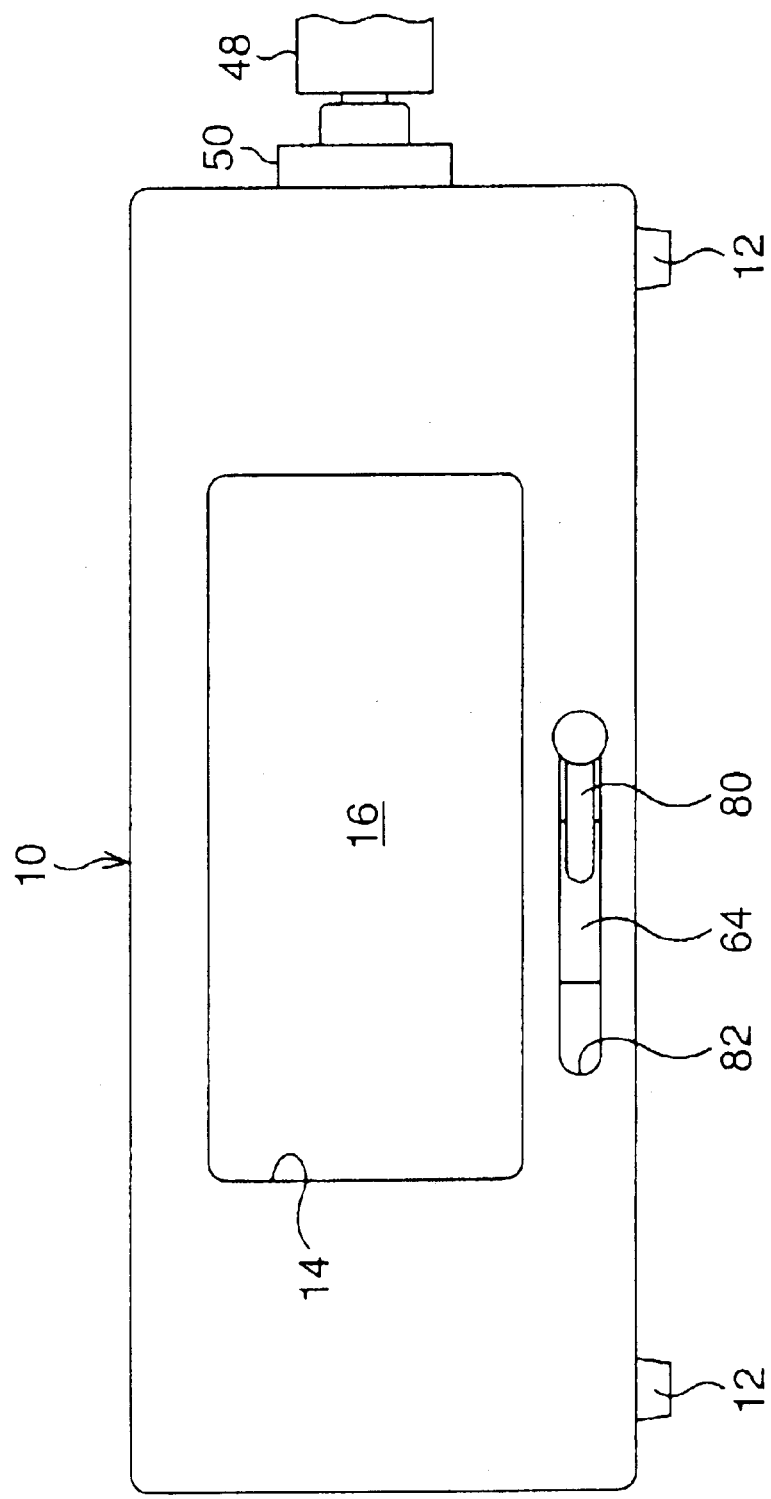
FIG. 8 is a side view of a light-source device of the second embodiment of the present invention.

As well as in the first embodiment, the light-source device 10 for an endoscope in the second embodiment is covered with the rectangular shaped housing 10. On the bottom surface of the housing 10, the hard rubber pads 12 are also attached to each of the four corners. Further, the lamp replacement window 14 is also formed on the sidewall of the housing 10 of the second embodiment. Usually, the lamp replacement window 14 is covered with the window cover 16, as shown in FIG. 8. However, the window cover 16 is removed from the window 14 when it comes time to replace a lamp, so that a user can access the inside of the housing 10 as shown in FIG. 9.

Figure 9:
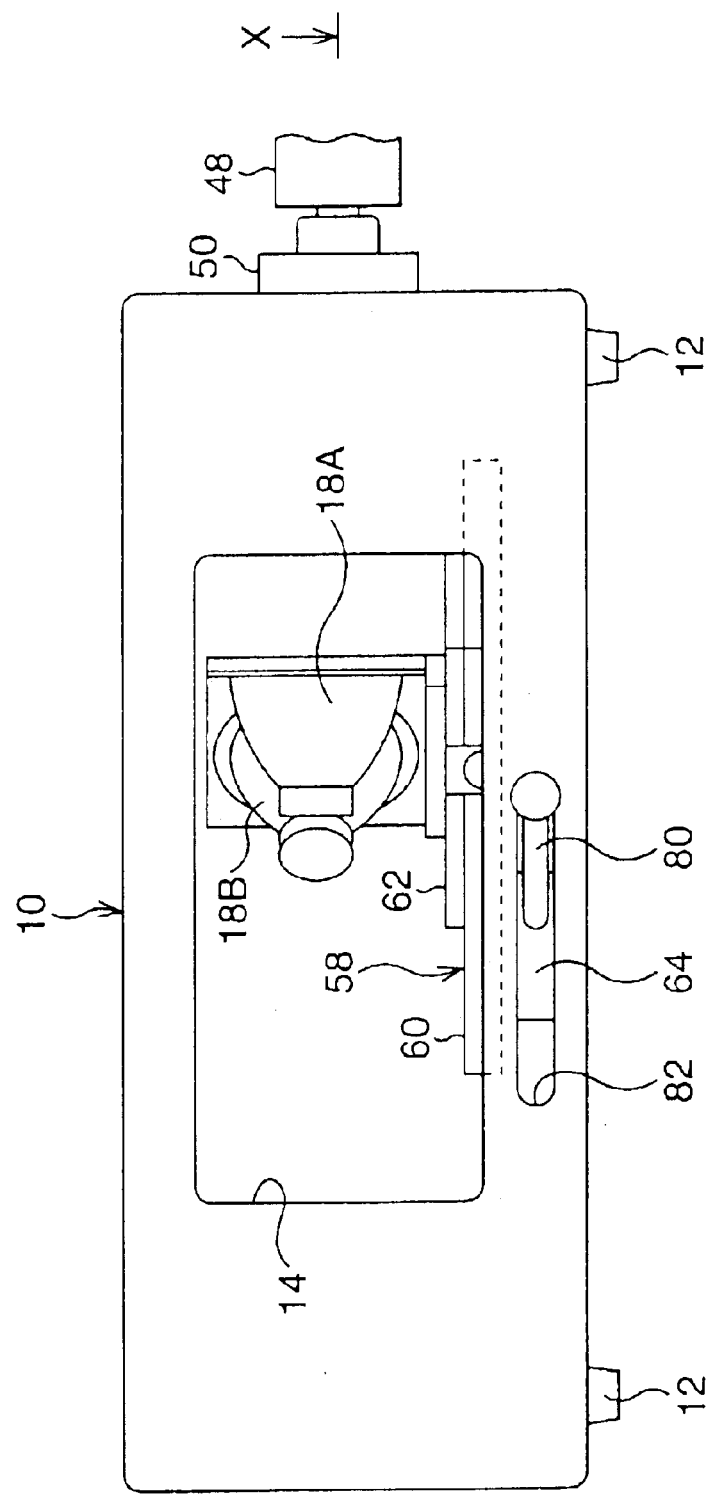
FIG. 9 is a side view of the light-source device in FIG. 8 with its window cover replaced and where the light-source unit inside the housing is visible.
Figure 10:
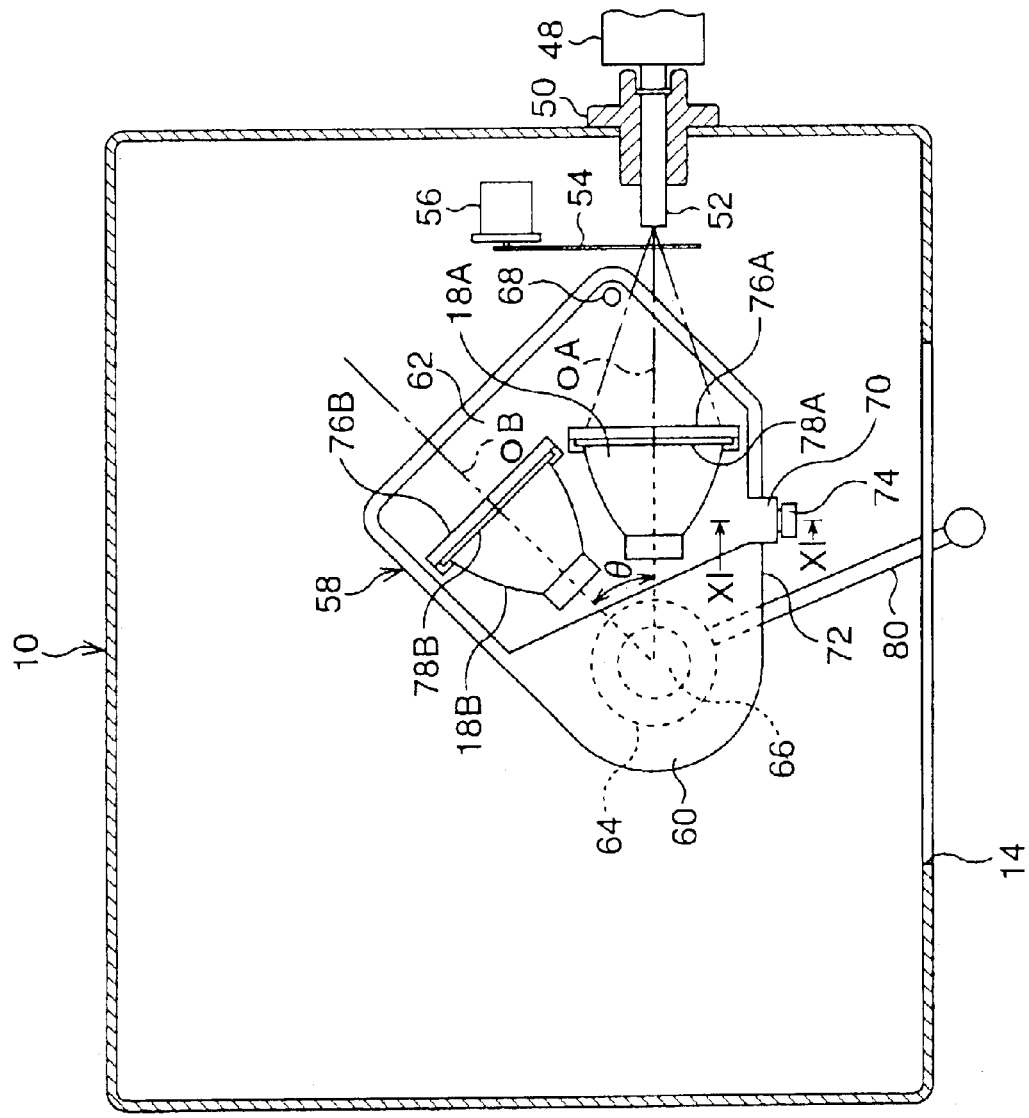
FIG. 10 is a cross sectional view of the light-source device along line X—X of FIG. 9 with the first movable lamp-mounting section at the first lamp position.

In FIG. 10, the light-source device is shown as a cross sectional view in which the housing 10 is sectioned along a line X—X of FIG. 9. As is clear from FIG. 9 and FIG. 10, in the second embodiment, there are provided two lamps 18A and 18B. As well as in the first embodiment, white lamps, such as a halogen lamp, xenon lamp, or the like, are also adopted for the lamps 18A and 18B, for example.

In the second embodiment, a lamp-mounting mechanism 58 (the numerate 58 integrally indicates the mechanism) that is for mounting the two lamps, such as the first and second white lamp 18A and 18B, is provided inside the housing 10. The lamp-mounting mechanism 58 comprises the first and second movable lamp-mounting sections 60 and 62. The first movable lamp-mounting section 60 is rotatable about a rotation axis perpendicular to the bottom inner surface 22 of the housing 10. The second movable lamp-mounting section 62 is disposed on the first movable lamp-mounting section 60 and is rotatable about a rotation axis perpendicular to the upper surface of the first movable lamp-mounting section 60.

In detail, the first movable lamp-mounting section 60 is formed as a rather thick board member with the profile shown in FIG. 10. A cylindrical sleeve 64 is formed on the bottom surface of the first movable lamp-mounting section 60. On the other hand, a rotation shaft 66 is perpendicularly fixed onto the bottom inner surface 22 of he housing 10, so that the first movable lamp-mounting section 60 is axially fixed on the rotation shaft 66 by the cylindrical sleeve 64. Thereby, the first movable lamp-mounting section 60 is rotatable about the central axis of the rotation shaft 66, that is, about the rotational axis perpendicular to the bottom inner surface 22 of the housing 10. Further, the second movable lamp-mounting section 62 is formed as a thin board member with a profile substantially the same as the profile of the movable lamp-mounting section 20 of the first embodiment. The second movable lamp-mounting section 62 is axially fixed to the first movable lamp-mounting section 60 by the pivot shaft 68 arranged at a corner of the second movable lamp-mounting section 62. Thereby, the second movable lamp-mounting section 62 is rotatable about the central axis of the pivot shaft 68, that is, about the rotational axis perpendicular to the upper surface of the first movable lamp-mounting section 60.

Note that, although it is not described in FIG. 10, a power source unit that supplies electric power to one of the white-light lamps 18A and 18B is provided inside the housing 10, as well as in the first embodiment. Further the power source obtains the power from a commercial power supply.

As is similar to the above described movable lamp-mounting section 20 of the first embodiment, a tongue piece member 70 extends out from the second movable lamp-mounting section 62 and its end is bent downward. When the second movable lamp-mounting section 62 is disposed at the lighting position, the end or the downwardly bent portion of the tongue piece 70 contacts with the peripheral side face 72 of the first movable lamp-mounting section 60. At the downwardly bent portion of the tongue piece 70, there is formed a through-hole through which a fastening screw 74 is inserted. The fastening screw 74 is screwed into the screw hole formed on the peripheral side face 72 of the first movable lamp-mounting section 60 via the through-hole, and fastened. Thereby, the second movable lamp-mounting section 62 is fixed at the lighting position with respect to the first movable lamp-mounting section 60, as shown in FIG. 10.

Figure 11:
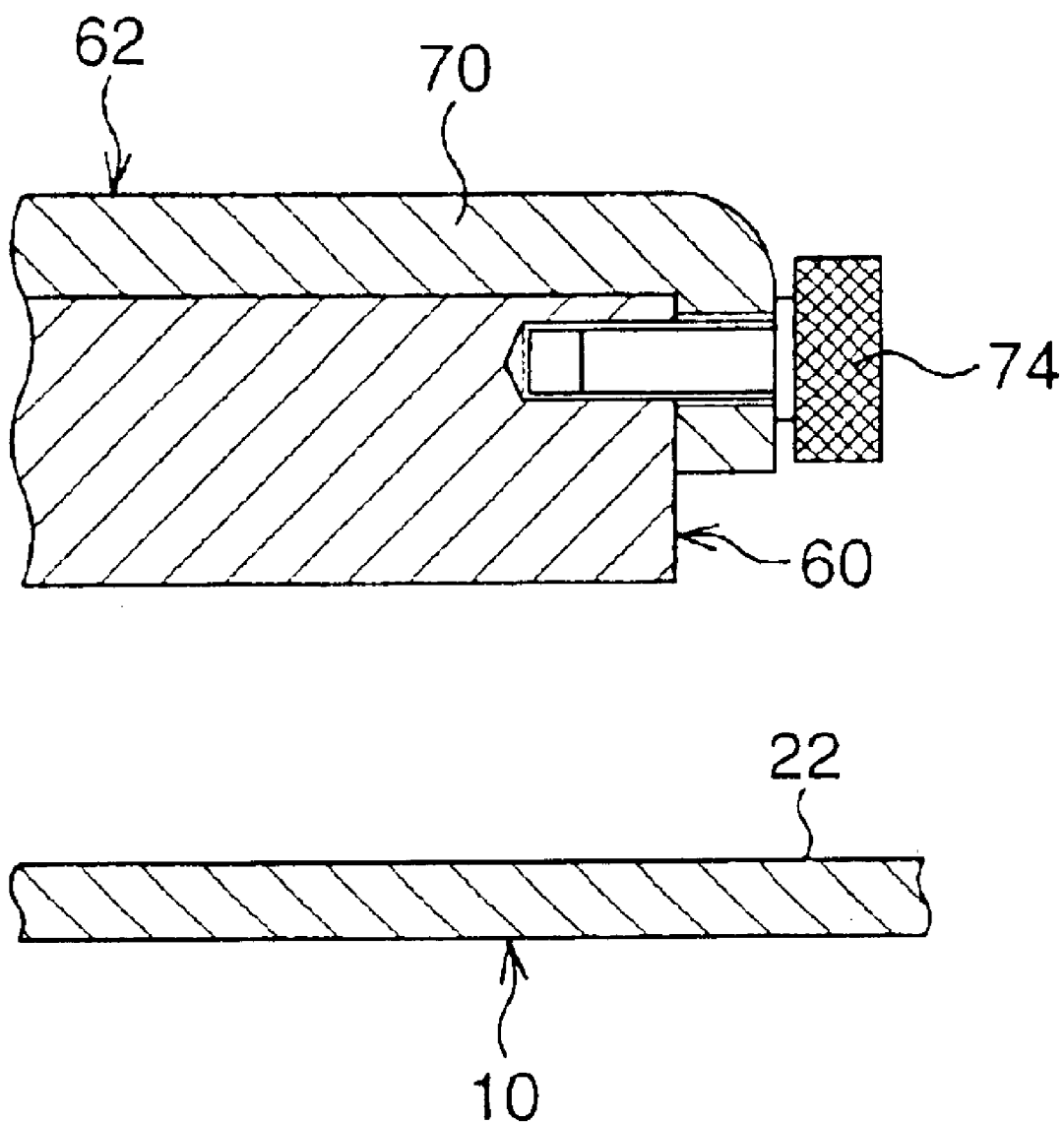
FIG. 11 is a magnified sectional elevational view showing the mechanism for fastening the second movable lamp-mounting section to the first movable lamp-mounting section along line XI—XI of FIG. 10.

As it is described in the first embodiment, the fastening screw 74 has a head with a large diameter, as shown in FIG. 11. Further, the head has a serration for preventing slipping on the periphery. Thereby, the fastening operation and the loosening operation by screwing the fastening screw 74 can be manually carried out. Namely, the fastening screw 74 fulfills the fixing function, to releasably fix the second movable lamp-mounting section 62 at the lighting position indicated in FIG. 10.

For mounting the respective first and second white lamps 18A and 18B to the second movable lamp-mounting section 62, lamp-mounting frames 76A and 76B are fixedly attached to the second movable lamp-mounting section 62. The lamp-mounting frames 76A and 76B are integrated with the fitting members 78A and 78B. Each of the lamp-mounting frames 76A and 76B and each of the fitting members 78A and 78B are substantially the same as the respective lamp-mounting frame 34 and fitting member 36 of the first embodiment (see FIG. 5 and FIG. 6). The mounting operations for each of the first and second white lamps 18A and 18B are carried out in a similar way to that described in the first embodiment with reference to FIG. 5 and FIG. 6.

In the second embodiment, two power supply sockets (not shown) are provided inside the housing 10. These two power supply sockets are plugged into each of the electrode plug pairs of the first and second white lamps 18A and 18B. The power supply sockets are connected to the power supply unit via electric cords. Note that, as well as in the above described first embodiment, a lamp power switch is provided on the outer surface of the housing 10 at a certain appropriate position. Namely, the ON/OFF state of the white lamps 18A and 18B is controlled by the lamp power switch according to requirements.

As is suitably illustrated in FIG. 10, as well as in the above first embodiment, on the sidewall of the housing 10, the connector 50 for connecting the illumination guide cable 48 is attached. At the incident end of the light guide cable 48, the optical guide rod 52 is optically connected, so that the light guide cable 48 is optically connected to the light-source device when the optical guide rod 52 is plugged into the connector 50.

Each of the first and second white lamps 18A and 18B is substantially same as the white lamp 18 used in the first embodiment. Namely, inside each of the white lamps (18A, 18B), a concaved reflecting mirror is installed, and their openings are provided with condensing lenses. In FIG. 10, the optical axis of the concaved reflecting mirror in the first white lamp 18A is indicated by a reference symbol OA, and the optical axis of the concaved reflecting mirror in the second white lamp 18B is indicated by a reference symbol OB. Further, extended lines for each optical axis OA and OB, that is the lines extending backward and forward from the first and second white lamps 18A and 18B, are indicated by broken lines. As is apparent from the figure, the lines extending from the optical axis OA and OB intersect at a predetermined angle θ on the central axis of the rotation shaft 66. Further, the first and second white lamps 18A and 18B are disposed at positions that are separate from the central axis of the rotation shaft 66, at the same distance.

In FIG. 10, the first movable lamp-mounting section 60 is indicated at the first lamp position. At this time, the optical axis OA of the concaved reflecting mirror of the first white lamp 18A coincides with the optical axis of the light guide rod 52 which is plugged into the connector 50 and being connected thereto. Further, the distal end of the light guide rod 52 is positioned at the focal point of the condensing lens of the first white lamp 18A. Accordingly, the light emitted from the first white lamp 18A is efficiently concentrated upon the end face of the light guide rod 52 and made incident thereto.

Figure 12:
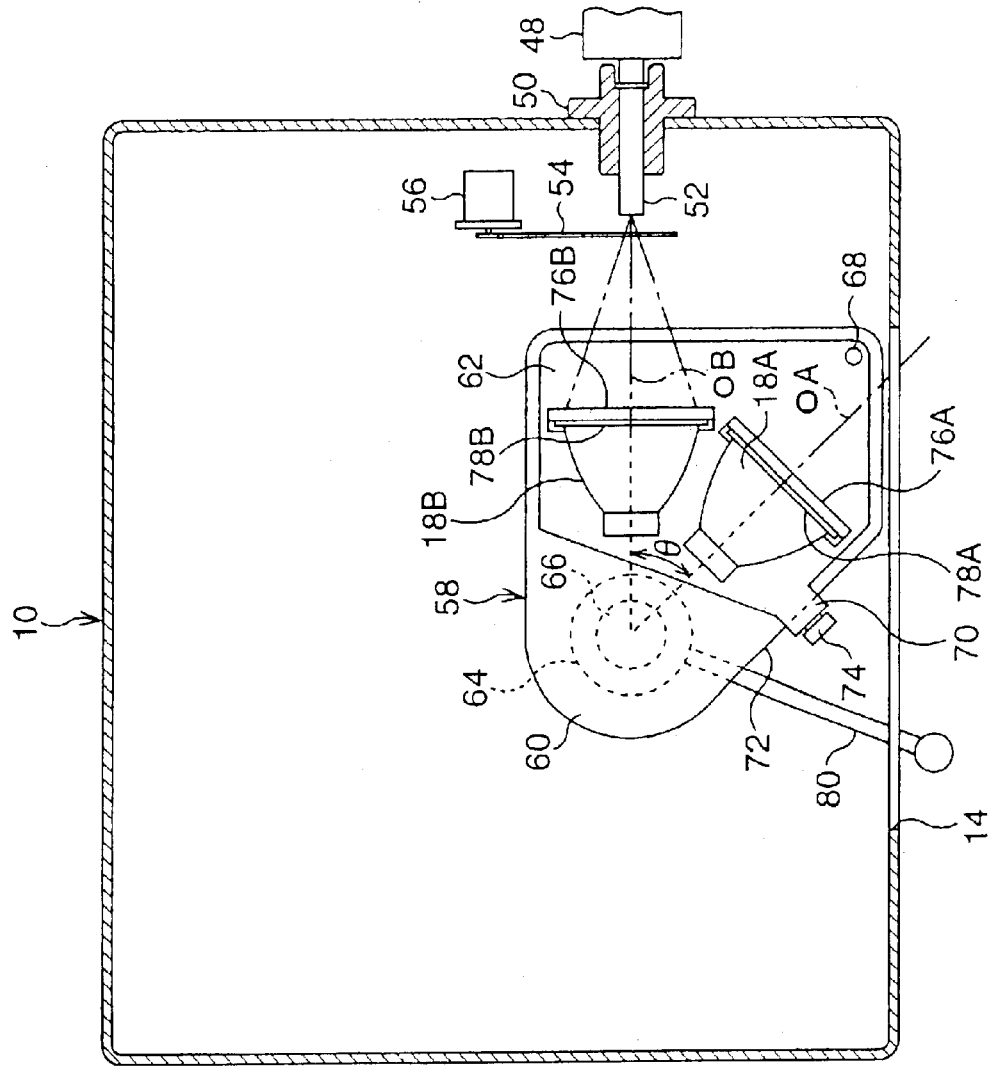
FIG. 12 is a cross sectional view of the light-source device along a line X—X of FIG. 9 with the first movable lamp-mounting section at the second lamp position.

Referring to FIG. 12, the first movable lamp-mounting section 60 is positioned at the second lamp position. This second lamp position corresponds to the position to which the first movable lamp-mounting section 60 being rotated clockwise at the angle θ from the first lamp position (FIG. 10). The first and second white lamps 18A and 18B are disposed in the above-described arrangement, the optical axis OB of the concaved reflecting mirror of the second white lamp 18B coincides with the optical axis of the light guide rod 52 which is plugged into the connector 50 and being connected thereto, when the first movable lamp-mounting section 60 is positioned at the second lamp position (FIG. 12). Further, the distal end of the light guide rod 52 is positioned at the focal point of the condensing lens of the second white lamp 18B. Accordingly, the light emitted from the second white lamp 18B is efficiently concentrated upon the end face of the light guide rod 52 and made incident thereto.

In the second embodiment, the transfer of the first movable lamp-mounting section 60 between the first lamp position (FIG. 10) and the second lamp position is manually carried out. Therefore, a handling lever 80 is attached to the cylindrical sleeve 64. The handling lever 80 radially extends from the cylindrical sleeve 64 and sticks out from the sidewall of the housing 10. Namely, as shown in FIG. 8 and FIG. 9, in the second embodiment, a narrow strip opening 82 is formed on the sidewall of the housing 10, along the bottom side of the housing 10, below the lamp replacement window 14, so that the handling lever 80 sticks outside the housing 10 through the opening 82. As described in the figures, at the end of the handling lever 80, a spherical grip is attached. The first movable lamp-mounting section 60 is transferred between the first lamp position (FIG. 10) and the second lamp position (FIG. 12) by means of manually operating the grip in the horizontal directions.

In order to ensure the positioning of the first lamp-mounting section 60 at the first and second lamp positions, a positioning mechanism is provided between the cylindrical sleeve 64 and rotation shaft 66. In the second embodiment, a part of the positioning mechanism is installed at the position where the handling lever 80 is attached to the cylindrical sleeve 64.

Figure 13:
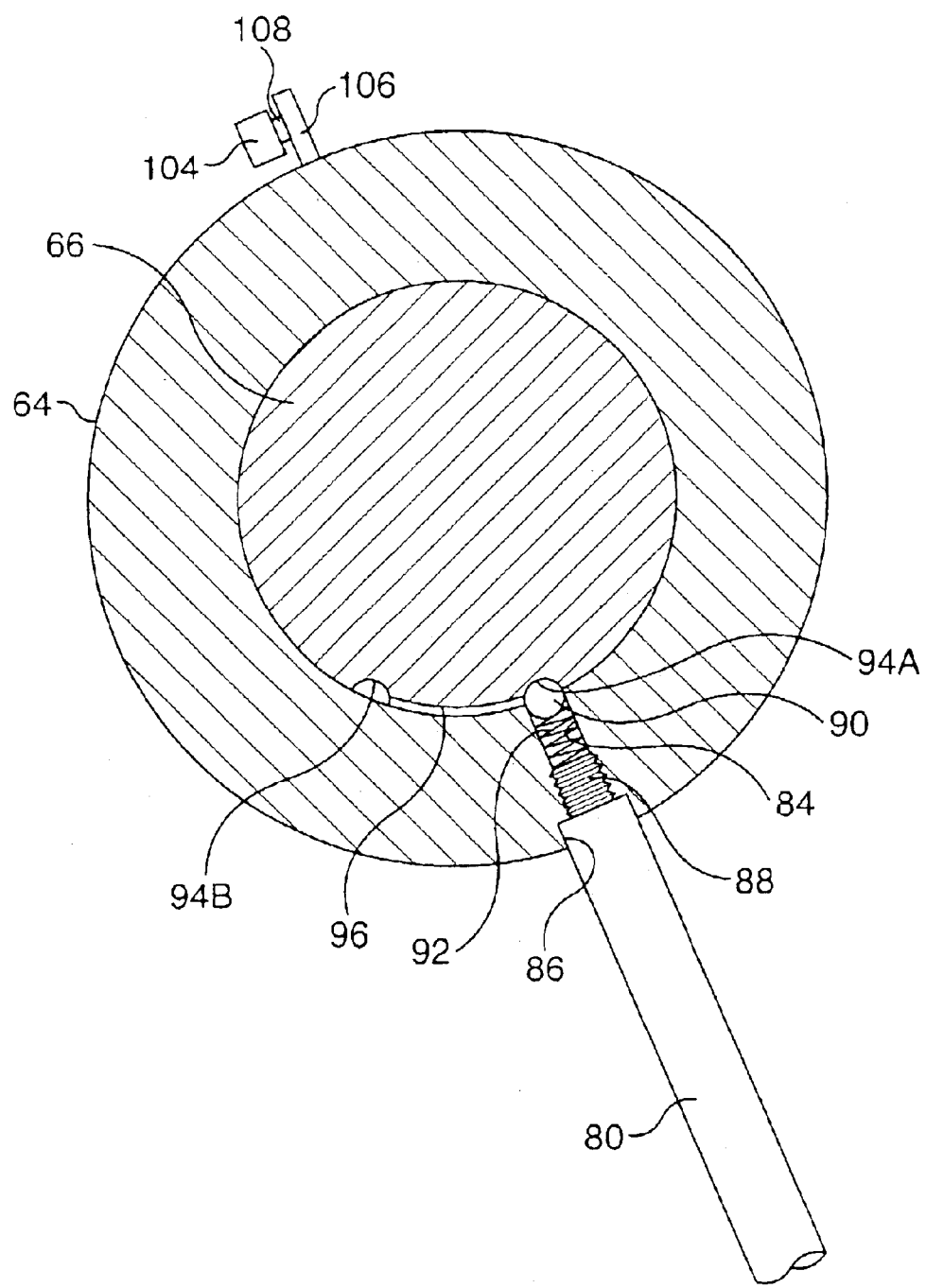
FIG. 13 is a sectional view of the cylindrical sleeve and the rotation shaft in the horizontal plane including the central axis of the handling lever when the first movable lamp-mounting section is positioned at the first lamp position.

Referring to FIG. 13, the sectional view of the cylindrical sleeve 64 and the rotation shaft 66 in the horizontal plane including the central axis of the handling lever 80 is illustrated. As indicated in the figure, a passing hole 84 is radially formed on the cylindrical sleeve 64. The outermost area of the passing hole 84 is provided with a large diameter portion 86 into which the end of the handling lever 80 is received. The outer half area of the passing hole 84 is formed as a female screw portion. On the other hand, a small diameter portion 88 protrudes out from the end face of the handling lever 80 as a male screw portion. The small diameter portion or the male screw portion 88 of the handling lever 80 is screwed into the female screw portion of the passing hole 84, so that the handling lever 80 is attached to the cylindrical sleeve 64.

The inside surface of the inner half area of the passing hole 84 is made smooth and a small ball 90 is slidably received inside the inner half area of the passing hole 84. Further a compressed coil spring 92 is arranged between end portion of the male screw portion 88 and the small ball 90. On the other hand, on the outer surface of the rotation shaft 66, first and second hemisphere hollows 94A and 94B are formed. An arc guide groove 96 is laid between the first and second hemisphere hollows 94A and 94B. Further, the first and second hemisphere hollows 94A and 94B are separately formed so as to make the angle θ between each other with respect to the central axis of the rotating shaft 66.

When the first movable lamp-mounting section 60 is positioned at the first lamp position (FIG. 10), the small ball elastically latches into the first hemisphere hollow 94A in accordance with the spring force of the compressed coil spring 92, as shown in FIG. 13. When the handling lever 80 is operated and the first lamp-mounting section 60 is moved from the first lamp position toward the second lamp position, the small ball 90 slips out the first hemisphere hollow 94A against the spring force of the compressed coil spring 92 and slides along the arc guide groove 96. When the first movable lamp-mounting section 60 reaches the second lamp position (FIG. 12), the small ball 90 is latched into the second hemisphere hollow 94B by the spring force of the compressed coil spring 92.

When the small ball 90 latches into the second hemisphere hollow 94B, it produces some braking impulse, so that this impulse is transmitted to an operator through the handling lever 80. Namely, the operator can sense the positioning of the first lamp-mounting section 60 at the second lamp position by the impulse. Thereby, the positioning of the first lamp-mounting section 60 at the second lamp position can be ensured. Note that, the same thing can be said when the first lamp-mounting section 60 is returned to the first lamp position (FIG. 10) from the second lamp position (FIG. 12 and FIG. 14).

Figure 15:
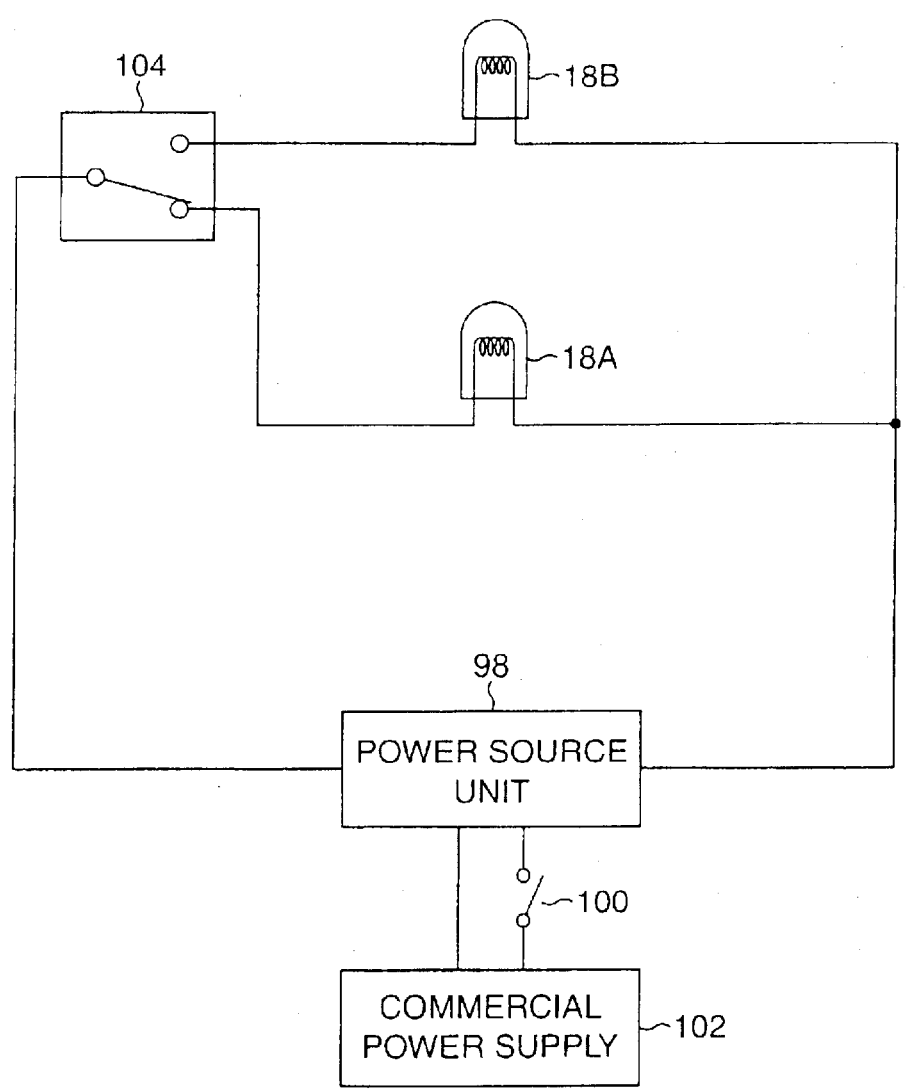
FIG. 15 is an electrical block diagram of a power supply circuit for the first and second white lamps.

With reference to FIG. 15, a power supply circuit for the first and second white lamps 18A and 18B is illustrated. When the first movable lamp-mounting section 60 is positioned at the first lamp position (FIG. 10), the power supply circuit selects the first white lamp 18A as the lamp to be turned on. On the other hand, when the first movable lamp-mounting section 60 is positioned at the second lamp position (FIG. 12), the power supply circuit selects the second white lamp 18B as the lamp to be turned on.

In FIG. 15, the power source unit installed inside the housing 10 is indicated by the numeral 98, and the lamp power switch provided on the appropriate position of the sidewall of the housing 10 is indicated by the numeral 100. The electric power is supplied to the power source unit 98 from the commercial, power supply 102 via the lamp power switch 100. Further, in FIG. 15, a power supply selector, which alternatively selects the lamp to be supplied with the electric power, that is between the first and second lamp 18A and 18B, is indicated by the numeral 104.

Figure 14:
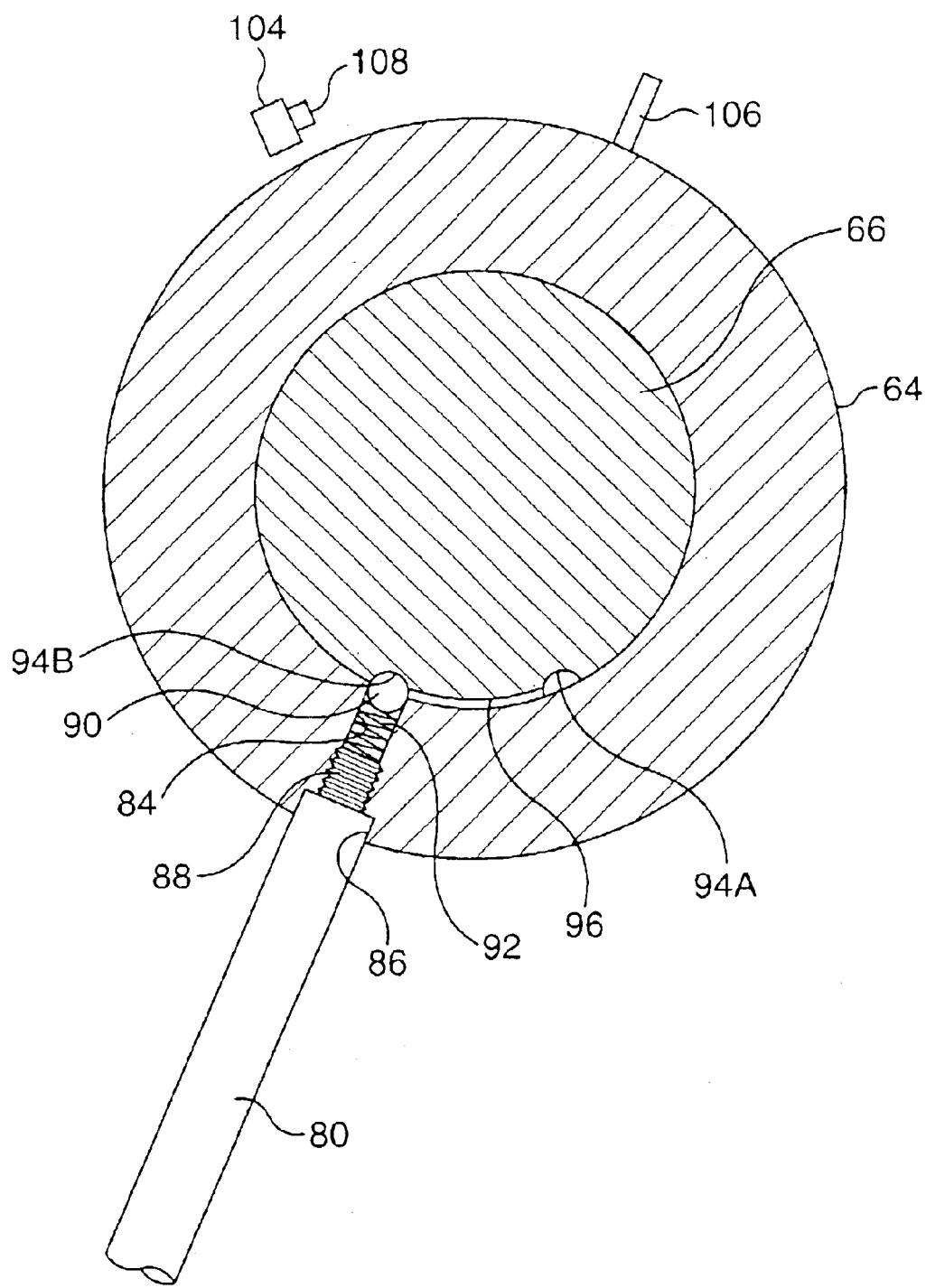
FIG. 14 is a sectional view of the cylindrical sleeve and the rotation shaft in the horizontal plane including the central axis of the handling lever when the first movable lamp-mounting section is positioned at the second lamp position.

As described in FIG. 13 and FIG. 14, the power supply selector 104 is disposed at an appropriate position nearby the cylindrical sleeve 64. This power supply selector 104 is operated by a rod 106 that protrudes toward the radial direction from the outer surface of the cylindrical sleeve 64. As is obvious from FIG. 15, the power supply selector 104 has a single pole double throw construction and has an operational button 108 which is given spring force to switch the contacts so that the electric power is supplied to the second lamp 18B without an external force on the operational button 108. When the first movable lamp-mounting section 60 is positioned at the first lamp position (FIG. 10 and FIG. 13), the operational button 108 is depressed by the rod 106 against the spring force. At this time, the power supply selector 104 is operated so as to supply power to the first white lamp 18A, as shown in FIG. 15, so that the first white lamp 18A can be turned on.

When the first movable lamp-mounting section 60 is positioned at the second lamp position (FIG. 12 and FIG. 14), the operational button 108 is released from the rod 106. At this time, the power supply selector 104 is switched so as to supply the power to the second white lamp 18B, so that the second white lamp 18B can be turned on.

Accordingly, even when the first white lamp 18A is burnt out during the endoscopy, the first white lamp 18A can be immediately switched to the second white lamp 18B by transferring the first movable lamp-mounting section 60 to the second lamp position (FIG. 12) from the first lamp position (FIG. 10). Thereby, the endoscopy can be resumed immediately.

How to exchange the first and second white lamp 18A and 18B in the second embodiment is explained in the following.

Figure 16:
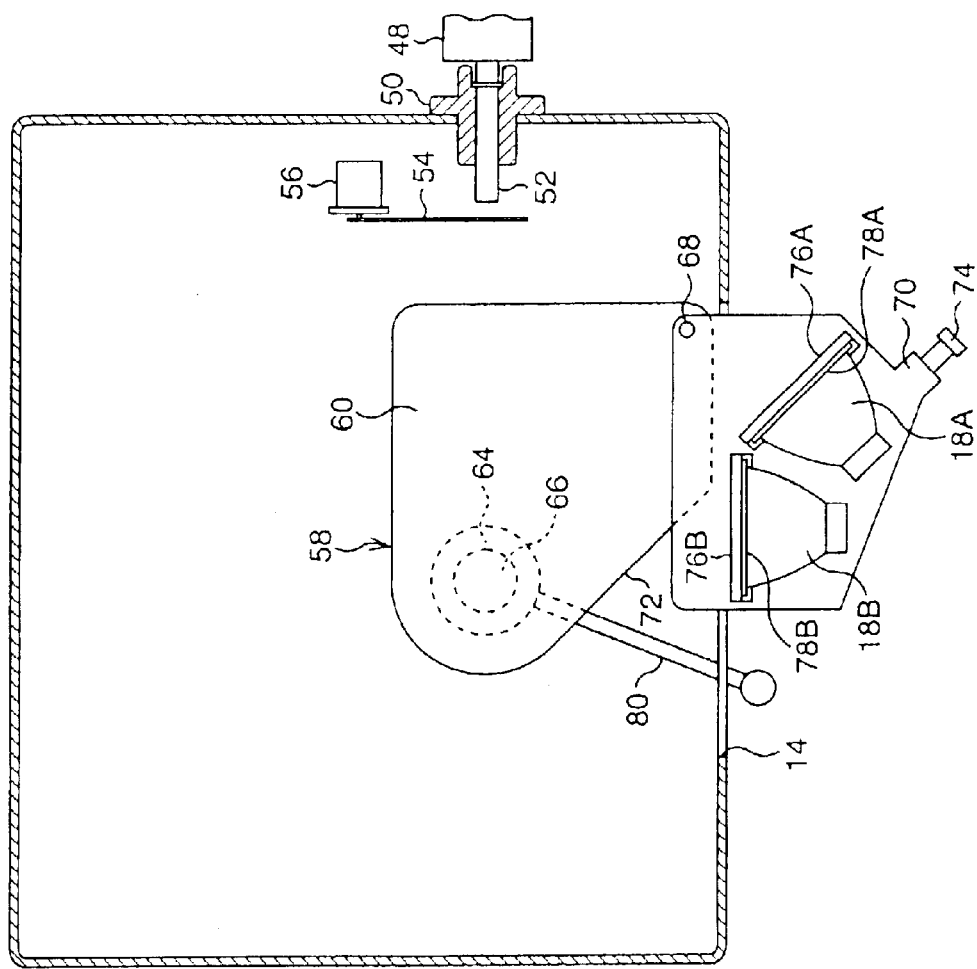
FIG. 16 is a cross sectional view of the light-source device along a line X—X of FIG. 9 with the second movable lamp-mounting section at the lamp replacing position.

As it similar to the first embodiment, the power source switch 100 is turned off at the beginning of the operation in order to safely carry out the replacement. The window cover 16 is then removed from the housing 10, so that the second movable lamp-mounting section 62 can be accessed through the lamp replacement window 14. At this time, whether the first movable lamp-mounting section 60 is positioned at the second lamp position is confirmed. When the fist movable lamp-mounting section 60 is positioned at the first lamp position, the first movable lamp-mounting section 60 is transferred to the second lamp position in order for the fasting screw 74 to be accessible. The fasting screw 74 is then detached from the screw hole by a manual unfastening operation. When the second movable lamp-mounting section 62 is rotated about the pivot shaft 68 by pulling the second movable lamp-mounting section 62 outwardly, the second movable lamp-mounting section 62 is moved from the lighting position to the lamp replacing position, which is shown in FIG. 16, with respect to the first movable lamp-mounting section 60. As is obvious from FIG. 16, the first and second white lamps 18A and 18B are pulled out to the outside of the housing 10 with the second movable lamp-mounting section 62 through the lamp replacement window 14.

Accordingly, either of the first and second white lamps 18A and 18B can be replaced a new one quite easily by pulling out the white lamps 18A and 18B to the outside of the housing 10. After replacing a burnt-out lamp of the two white lamps 18A and 18B with a new one, the second movable lamp-mounting section 62 is withdrawn to the lighting position by carrying out the above processes in reverse. The second movable lamp-mounting section 62 is then positioned at either of the first and second lamp positions, thus one of the first or the second white lamps 18A, 18B is made available for use.

In the above-described second embodiment, although two white lamps 18A and 18B are mounted on the second lamp-mounting section 62, more than two white lamps can be mounted on the second lamp-mounting section 62. In this case, the first movable lamp-mounting section 60 is structured so that it can be positioned at each of the lamp positions that corresponds to the respective white lamps mounted on the second movable lamp-mounting section 62. Namely, the number of the lamp position is equal to the number of lamps mounted on the second movable lamp-mounting section 62.

Further, in the first and second embodiments, the window cover 16 is removed form the housing 10 when carrying out the lamp replacement, the window cover 16 may be structured as a hinged door or other type.

Furthermore, the light-source device of the present invention can not only used with an optical fiber scope but can also be used with an electronic endoscope by integrating the light-source device with an image-signal processing unit, that is, as an image-signal processing apparatus for an electronic endoscope. In FIG. 17, the structure of the image-signal processing apparatus is schematically shown, as an example. Inside the housing 10', the light-source device and the image-signal processing unit 200 are provided. The construction of the light-source device is the same as that in the first embodiment. The image-signal processing unit 200 receives image signals from the CCD mounted at the distal end of an electronic endoscope. The image signals are subjected to a predetermined image processing in the image-signal processing unit 200 and are then fed to a monitor. Of course, the light-source device in the second embodiment can also be applied to the above image-signal processing apparatus.

As described above, according to the light-source device in the present embodiments of the invention, the lamp can be pulled outside the housing when the replacement of the lamp is required. Therefore, replacement of the lamp can be efficiently and swiftly carried out. Further, as in the second embodiment, when the light-source device is provided with at least two selective lamps, an endoscopy can be substantially continued without interruption, since one lamp can be switched for another even when the former is burnt out.

Further, in the present embodiments, a white lamp is used for an example, however, any other color or type of lamp can be used in the present embodiments.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2002-098717 (filed on Apr. 1, 2002) which is expressly incorporated herein, by reference, in its entirety.

What is claimed is:

1. A light-source device for an endoscope, comprising:
   a housing in which a lamp replacement opening is formed;
   a first lamp and a second lamp that are mounted inside of said housing; and
   a first movable lamp-mounting section that is transferable with respect to said housing, between a first lamp position and a second lamp position; and
   a second movable lamp-mounting section, to which said first and second lamps are mounted, which is attached to said first movable lamp-mounting section such that said second movable lamp-mounting section is transferable between a lighting position and a lamp replacing position with respect to said first movable lamp-mounting section;
   wherein said first lamp is optically connectable to a light guide cable, which transmits illumination light to said endoscope, when said second movable lamp-mounting section is positioned at said lighting position and when said first movable lamp-mounting section is positioned at said first lamp position, and said second lamp is optically connectable to said light guide cable when said second movable lamp-mounting section is positioned at said lighting position and when said first movable lamp-mounting section is positioned at said second lamp position, and further said first and second lamps are positioned outside of said housing when said second movable lamp-mounting section is pulled out to said lamp replacing position through said lamp replacement opening.

2. A light-source device according to claim 1, further comprising a fixing mechanism that releasably fixes said second movable lamp-mounting section to said first movable lamp-mounting section at said lighting position.

3. A light-source device according to claim 1, further comprising a selector that selects one lamp, of said first and second lamps, to be turned ON, wherein said first lamp is selected when said first movable lamp-mounting section is positioned at said first lamp position and said second lamp is selected when said first movable lamp-mounting section is positioned at said second lamp position.

4. A light-source device according to claim 1, further comprising a handling lever configured to transfer said first movable lamp-mounting section between said first and second lamp positions, and wherein said handling lever is connected to said first movable lamp-mounting section and extends outwardly from said housing through an opening formed in said housing.

5. A light-source device according to claim 4, further comprising a latch mechanism that ensures positioning of said first movable lamp-mounting section at said first and second lamp positions when said first movable lamp-mounting section is being moved by said handling lever.

6. A light-source device according to claim 5, wherein said latch mechanism is structured so as to provide a predetermined amount of biasing to said handling lever when said first movable lamp-mounting section is positioned at one of said first lamp position and said second lamp position.

* * * * *